United States Patent [19]
Parliment et al.

[11] 3,962,321
[45] *June 8, 1976

[54] ENHANCEMENT OF COFFEE FLAVOR

[75] Inventors: Thomas H. Parliment, Valley Cottage; William P. Clinton, Monsey, both of N.Y.; Richard Scarpellino, Ramsey, N.J.; Robert J. Soukup, New City; Martin F. Epstein, Pearl River, both of N.Y.

[73] Assignee: General Foods Corporation, White Plains, N.Y.

[ * ] Notice: The portion of the term of this patent subsequent to Apr. 11, 1989, has been disclaimed.

[22] Filed: Dec. 17, 1973

[21] Appl. No.: 425,366

Related U.S. Application Data

[60] Division of Ser. No. 243,055, April 11, 1972, Pat. No. 3,886,297, which is a continuation-in-part of Ser. No. 129,609, March 30, 1971, Pat. No. 3,655,397, which is a continuation-in-part of Ser. No. 867,887, Oct. 12, 1969, abandoned, which is a continuation-in-part of Ser. No. 857,227, Sept. 11, 1969, abandoned.

[52] U.S. Cl. .............................. 426/535; 426/537
[51] Int. Cl.² ...................................... A23L 1/234
[58] Field of Search ............ 426/65, 175, 535, 537

[56] References Cited
UNITED STATES PATENTS

| | | | |
|---|---|---|---|
| 3,655,397 | 4/1972 | Parliment et al. | 426/175 |
| 3,702,253 | 11/1972 | Winter et al. | 426/175 UX |

*Primary Examiner*—Joseph M. Golian
*Attorney, Agent, or Firm*—Bruno P. Struzzi; Daniel J. Donovan; Thomas R. Savoie

[57] ABSTRACT

Enhancement of the coffee flavor of foodstuffs is achieved by the addition of a small but effective amount of a mixture of a) 2-nonenal, and/or 2-nonenol and particular derivatives thereof; and b) a compound represented by

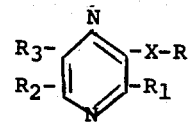

where X is oxygen or sulfur, R is lower alkyl, and $R_1$, $R_2$, and $R_3$ is hydrogen or alkyl provided at least one of $R_1$, $R_2$, and $R_3$ is alkyl of two to twelve carbons.

13 Claims, No Drawings

3,962,321

ENHANCEMENT OF COFFEE FLAVOR

This application is a Divisional Application of U.S. Pat. application Ser. No. 243,055, filed Apr. 11, 1972 now U.S. Pat. No. 3,886,297, patented May 27, 1975 which in turn is a Continuation-in-part of U.S. Pat. application Ser. No. 129,609, filed Mar. 30, 71 now U.S. Pat. No. 3,655,397, patented Apr. 11, 1972 which in turn is a Continuation-in-part of Ser. No. 867,887, Oct. 12, 1969, abandoned, which is a Continuation-in-part of Ser. No. 857,227, Sept. 11, 1969, abandoned.

BACKGROUND OF THE INVENTION

1. Field of the Invention

The present invention relates to 2-nonenal, and 2-nonenol, woody flavor compounds found to be useful in the area of flavor note alteration whether by the enhancement of flavor or flavor notes that are characteristic in a substance, by modification of a flavor or flavor note from a less to a more desirable one, or by the complete or partial masking of a flavor or flavor note. Still more particularly, the invention relates to incorporation of the above-mentioned compounds and mixtures threeof in food to reduce the caramel, acid and sour flavor of food, and modify and improve the green, earthy and buttery notes of coffee, and add a desirable woody, flavor note to foodstuffs.

2. Description of the Prior Art

In the field of flavor enhancement, it has been general practice to employ synthetic and naturally isolated compounds and compositions to enhance and/or mask the flavor of foodstuffs. The enhancement of flavor is extremely complex, each individual flavor containing literally hundreds of compounds, each of which produces, to some degree, a flavor impact. In general, the isolation of a single flavor does not allow one to predict eqivalent flavors, since compounds of greatly differing structure have been found to produce approximately the same flavor character, while compounds of similar structure frequently differ appreciably in taste. Consequently, the identification of desirable flavor components requires synthesis and trial of individual candidates until compounds are identified which have desirable flavor notes.

In the area of flavor enhancement of coffee flavored foodstuffs, especially soluble spray dried and freeze dried coffee and regular coffee, thousands of compounds have been screened over the years in an attempt to isolate desirable components of coffee flavor. For many years, coffee technologists have searched for a flavor enhancing compound which would produce the flavor note generally described by experts as woody.

Trans-2-nonenal and trans-2-nonenol are old compounds, but their presence in coffee has not apparently been reported.

Trans-2-nonenal is formed from the oxidative fission of the hydroperoxide of methyl oleate and is found in the essential oil of Achasma walang Val and in cranberries, cucumbers and carrots. 2-nonenal is suggested as a GRAS substance among many others in Food Technology, Vol. 24, pp 533–41, May 1970.

Synthesis of trans-2-nonenol, trans-2-nonenal and its acetals have been reported in the literature.

Organoleptically, we suspected that either trans-2-nonenal or trans-2-nonenol were present in certain fractions of coffee, such as percolated, roasted and ground brew, roasted coffee oil, and steam generated roasted and ground coffee aroma. The similarity of the woody flavor of these coffee fractions and trans-2-nonenal and trans-2-nonenol is apparent to expert tasters.

We have recently found trans-2-nonenal to be present in Columbian green and roasted coffee as well as aroma fractions of roasted coffee.

The presence of woody compounds, which are the subject of this invention, in soluble coffee, especially spray dried soluble, is unlikely since flavor experts organoleptically do not detect a woody flavor or aroma in these coffees.

Trans-2-nonenal is characterized by flavor experts to have an unpleasant, rancid fat flavor when tasted at conventional flavor concentrations of 50 ppm or higher. Trans-2-nonenol has similar fatty characteristics as does cis-2-nonenol. The acetals and esters have a fatty flavor but at much higher levels exceeding one part per million. Aroma quality is judged as pungent and unpleasant at the fatty flavor concentrations.

SUMMARY OF THE INVENTION

The general purpose of this invention is to provide 2-nonenol and 2-nonenal compounds and compositions which will enhance the flavor of foodstuffs.

The flavor enhancement is achieved by the addition of a small but effective amount of 2-nonenal, 2-nonenol, lower alkyl acetals of 2-nonenal, esters of organic acid anhydrides and 2-nonenol in which the carbonyl group is not conjugated with a double bond or aromatic ring and mixtures thereof to the food to be flavored.

The 2-nonenal, 2-nonenol and mixtures thereof produce a coffee flavor when added in minute amounts (well below 25 ppm and generally in the range of 0.05 to 16 ppb) to water or foodstuffs. The acetal derivatives give a similar woody flavor at the previously mentioned concentrations but do not exhibit fatty undesirable flavor until levels of one part per million (ppm) are approached. The ester derivatives have a higher threshold flavor level of about 50–100 ppb with fatty flavor apparent in the parts per million concentration. In one respect, the derivatives are advantageous as flavoring agents since a wider range of woody flavor concentrations are possible. The woody flavor compounds of this invention mask typically undesirable flavors, balance overall flavor and impart a regular coffee flavor generally described by experts as woody.

The ability of the woody flavor compounds to produce a woody flavor and to balance and/or hide undesirable flavors is unexpected. These compounds, when incorporated at conventional flavor levels in foodstuffs, produce a flavor characterized by experts as an unpleasant cucumber, green fatty to rancid fat flavor totally unsuitable for coffee. Only at extremely low concentration is the woody flavor apparent and useful.

Foodstuffs including beverages which can be flavored with the flavoring agent of this invention include, for instance, ice cream; confectionery goods such as boiled sweets, hard candy, fillings, fondants, jellies and the like; meat products; custards; yogurt; milk drinks; syrups; carbonated beverages; spirits; liqueurs gelled deserts including gelatin deserts, cereal based beverages and the like.

The woody flavored compounds of this invention, and mixtures thereof, can be employed to contribute a slightly woody flavor to foods such as cola, ginger ale and other beverages, both carbonated and non-car bonated. They are employed at concentrations below the flavor threshold to mask or hide undesirable flavors or to enhance flavors desirable in the food treated.

It is an object of this invention to provide a flavoring agent which is capable of imparting a woody flavor and aroma to foodstuffs including beverages.

A further object of this invention is to provide an enhancing agent which can be added to naturally or synthetically flavored foodstuffs in order to improve or enhance the flavoring properties thereof and make more natural their flavor and aroma.

Another object of this invention is to provide foodstuffs having enhanced flavor and aroma.

Still another object of this invention is to provide a method for enhancing the flavor of foodstuffs.

DESCRIPTION OF THE INVENTION

The compounds employed in the compositions and processes of this invention are:

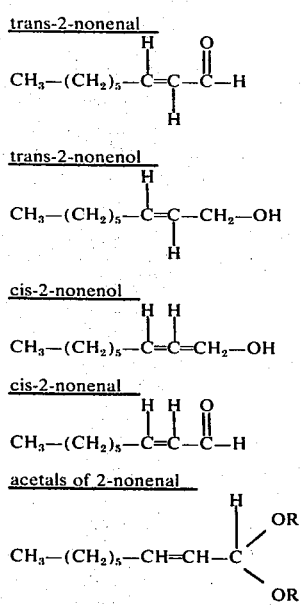

Where R is lower alkyl.

esters of organic acids and 2-nonenol in which the carbonyl is not conjugated with a double bond or aromatic ring.

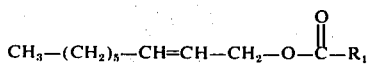

Where $R_1$ is hydrogen or lower alkyl or substituted lower alkyl.

Trans-2-nonenal and the trans-2-nonenal acetals are obtained by the process described by Paul Z. Bedoukian, Preparation of α, B-Unsaturated Aldehyde Dimethyl Acetals and Their Free Aldehydes, J.A.C.S., 79, 889–92 (1957).

The saturated aldehyde is converted to the enol acetate and then brominated in carbon tetrachloride. On adding methanol to the brominated mixture, the dimethyl acetal of a-bromo-aldehyde is obtained. On treatment of the latter with potassium hydroxide in butanol there is obtained the unsaturated acetal which is converted to the α, B-unsaturated aldehyde by acid hydrolysis. If desired, the aldehyde can be reduced using lithium aluminum hydride to the corresponding α, B-unsaturated alcohol.

Trans-2-nonenal is also prepared by the reduction of the imide chloride of a-nonenoic acid, Ber., 67B, 269 (1934); the hydrolysis of 1,1-dichloro-3-bromonanane, J.O.C. 13,895 (1948), U.S. Pat. No. 2,574,832; by the oxidation of the corresponding alcohol, Bull. soc. chim. 53, 301 (1933), J.A.C.S. 70, 2601 (1948); and by the oxidation of 9,10,12-trihydroxy stearic acid, J.A.C.S. 62, 2305 (1940).

Trans-2-nonenol is prepared via the Knovenagel condensation using n-heptanal and monoethyl malonate to give ethyl 2-nonenoate. Reduction of this ester with $LiAlH_4$ followed by hydrolysis gives the unsaturated alcohol (J.A.C.S. 70, 2601 (1948)). If desired, the alcohol can be oxidized to trans-2-nonenal by dichromate.

The acetals are prepared as per the method given in Advanced Organic Chemistry, R. C. Fuson, p. 368, John Wiley & Sons, (1950). The unsaturated aldehyde is treated with an alcohol in the presence of an acidic catalyst such as ammonium chloride, boron trifluoride etherate, p-toluenesulfonic acid or the like. Cyclic acetals or dioxolanes are formed by 1,2-glycols such as ethylene glycol which react with the unsaturated aldehyde to yield the dioxolane. The α, B-unsaturated aldehyde dimethyl acetals were prepared according to the procedure of P. Bedoukian, J.A.C.S., 79, 889–92 (1957).

The cis-2-nonenol is prepared by hydrogenation of commercially available 2-nonyn-1-ol using a Lindlar type catalyst as per D. Cram and N. Allinger, J.A.C.S., 78, 2518 (1956).

The cis-2-nonenal is prepared according to the procedure of Thomas and Warburton, J.C.S., p. 2988 (1965).

The esters of organic acid anhydrides and 2-nonenol are prepared by reaction of the alcohol with anhydride in pyridine following the procedure given in Wayner and Zook, p. 483, Synthetic Organic Chemistry, John Wiley & Sons (1953).

The following synthetic procedures are applicable to the synthesis of some of the preceeding compounds: Helv. Chim. Acta. 39, 1299 (1956); Compt. Rend. 247, 1627 (1958); Helv. Chim. Acta. 41, 1603 (1958); Gass. Chim. Ital. 88, 296 (1958); Chem & Ind. 202 (1960); and J.C.S. 1266 (1961).

2-nonenal, 2-nonenol, 2-nonenal dialkyl acetals and esters of organic acid and 2-nonenol in which the carbonyl is not conjugated with a double bond or aromatic ring are employed as woody flavoring compounds. The trans- form of the compounds are preferred woody flavoring agents particularly the alcohol and acetals. The woody flavor compounds are useful for enhancing the flavor of food.

Nonenal, nonenol and derivatives of this invention are useful for enhancing the flavor of food, either by producing a woody flavor, or by reducing undesirable flavors in various products or by increasing desirable flavors.

For example, when added to whisky, such as scotch, the wood compounds contribute an excellent flavor. When added to carbonated and non-carbonated beverages, trans-2-nonenal and trans-2-nonenol produce a low level woody note not detectable as coffee flavor which enhances the basic flavor of the beverage. Cola beverages are more like "Coke," a woody character in root beer improves it appreciably, etc.

In many foodstuffs the addition of the woody compounds of this invention to the food reduces undesirable notes. For example, in cranberry juice or jelly the compounds reduce astringency, and in synthetic flavored desserts and candies eliminate the cheap, candy character and produce a smoother, improved, more natural flavor. In sweet products such as maple flavored syrup, they enhance the flavor and make the product smoother in taste.

In many foods the woody compounds increase desirable flavors. For example, beverages, as noted previously, exhibit a smoother and more natural flavor. This is also true for puddings and other confections such as ice cream, sherbert, candy and the like. In meat products, such as fresh meat, broth, soups, hamburger and the like, the compounds produce a higher flavor impact and give the product a more meaty character.

The woody compounds are particularly useful for enhancing the flavor of cereal based beverages prepared from roasted cereals such as wheat, rye, barley and the like which have been processed to form a solubilized product. One such product, marketed under the trademark "Postum either regular or coffee flavored is a dried water extract of roasted wheat, barley and molasses (see U.S. Pat. No. 3,021,218). The woody compounds reduce the molasses (caramel) flavor, characteristic of Postum and at proportions above threshold level additionally contribute a woody coffee like flavor. They enhance coffee flavored food stuffs, where a regular coffee note characterized by coffee experts as woody is desired but deficient, such as some regular coffee like Robustas, decaffeinated coffee, soluble coffee, coffee flavored icing, coffee flavored carbonated and non-carbonated soft drinks, coffee flavored beverages produced from non-coffee raw materials such as Postum brand beverage, coffee flavored desserts such as gelatin, ice cream, pudding, cakes, cookies and the like, coffee flavored candies and the like, and other foodstuffs which have in part a coffee flavor such as mocha flavored foodstuffs. In addition, these compounds can be employed in foodstuffs normally used with coffee, such as coffee creamers, sweeteners, and the like, to impart a coffee flavor.

The woody compounds employed in this invention and mixtures thereof give a coffee flavor when added to water or foodstuffs in minute amounts. In addition to imparting a coffee like flavor having a strong woody note, these compounds exert a balancing effect on other desirable coffee notes such as the green, earthy and buttery notes, while masking the undesirable acid, sour and caramel notes.

In spray dried soluble coffee, the woody compounds and mixtures thereof enhance the woody character of the brew, while masking the caramel flavor. In addition, they exert a desirable blending effect on the overall brew flavor.

In freeze dried soluble coffee, the woody compounds and mixtures thereof contribute a woody note, and blend the winey, buttery notes, giving a more balanced flavor while hiding sourness.

Similar effects are noted when the preceding compounds are added to prelightened soluble coffee, or when incorporated with roasted and ground regular coffee.

When incorporated with foodstuffs containing other added coffee flavor fractions, both synthetic and those obtained from coffee, the woody compounds and mixtures thereof enhance coffee flavor by balancing the other flavors and by strengthening the woody regular coffee flavor which is deficient.

Depending on the flavor desired, the woody compounds or mixtures thereof can be incorporated in the foodstuff either alone or combined with other flavor ingredients and/or carriers.

It is particularly preferred to add a small but effective amount of the 2-nonenal and 2-nonenol woody flavored compounds to soluble coffee which is deficient either partially or totally in woody flavor to enhance the overall flavor. Addition may be either to the regular coffee prior to extraction, the extract prior to drying, or may be plated on or mixed with the dry coffee. Since only a minute amount of the flavor and aroma compounds is needed, it is preferred to incorporate them in an edible carrier or concentrate.

Because of the extremely low level of the unsaturated woody compounds necessary for enhancing food, it is preferred to form a concentrate which may then be incorporated in the foodstuff. The concentrate may be a liquid, syrup or solid, depending on its ultimate use.

The unsaturated alcohol or aldehyde and their woody derivatives may be incorporated in ethanol, propylene glycol, oils such as cottonseed, coffee, peanut or the like, or other edible vehicles to form a concentrate for convenient shipping, storage and addition to the foodstuffs. For example, oil--either coffee or other vegetable oil--containing the woody flavor compounds or mixtures thereof may be plated on soluble coffee to enhance its flavor, or alternatively the oil containing the flavor compound may be incorporated in extract and dried to form an enhanced soluble coffee.

Dry concentrates containing the woody compounds and mixtures thereof may also be prepared employing film forming compositions such as gums like gum arabic, pectins, alginates and the like, starch breakdown products such as Capsul (National Starch), Morex 1918 (Corn Products), Maltrin 10 (Grain Processing) and the like, candy melt systems and other art recognized stabilizing or diluent systems.

In forming any concentrate, the proportion of woody flavor compound or mixtures thereof in the concentrate is not critical, provided the level of flavoring is controlled to provide for even distribution of the flavor concentrate throughout the foodstuff to be flavored.

Minute amounts of the woody flavor 2-nonenal and 2-nonenol compounds or mixtures thereof are sufficient to produce an enhancement of coffee flavor in foodstuffs. For example, in a regular or soluble coffee beverage, say from about 1 to 1.5% coffee solids brew, the following flavor and aroma characteristics, defined by expert tasters, have been noted:

| Flavoring | Threshold Level | Recognition Level | Undesired Fatty Flavor Becoming Apparent |
|---|---|---|---|
| | ppb | ppb | ppb |
| cis-2-nonenol | 0.3 | 0.5 | 34 |
| trans-2-nonenal | 0.05–0.2 | 0.4–0.6 | 16 |
| trans-2-nonenol | 0.10–0.2 | 0.6 | 16 |
| trans-2-nonene dimethyl Acetal | 0.03 | 0.08 | 800 |
| trans-2-nonene diethyl acetal | 0.02 | 0.03 | 1200 |
| 1-Octenyl-1-dioxolane | 0.3 | 0.8 | 1000 |
| trans-2-nonenylacetate | 100 | 200 | 1500 |
| cis-2-nonenyl acetate | 50 | 150 | 1500 |

The threshold level is that quantity of flavoring producing a change in cup flavor and aroma, but a change which cannot be described as a particular flavor. The recognition level is the quantity of flavoring which can be defined as imparting a woody note to the brew. The fatty level is that point where the undesirable fatty flavor becomes apparent and detracts from the woody character of the flavoring noted at lower levels. For coffee brew from 0.01, and more preferably from 0.05 parts per billion (ppb) of the woody flavor compounds and mixtures thereof are employed. Generally, there is employed in the brew from 0.05 ppb to 16 ppb, with 0.1 ppb to 5 ppb preferred. A very desirable concentration for most of the 2-nonenal and 2-nonenol woody flavored compounds which exert a balancing of desirable regular coffee flavor, imparts woodiness and masks undesirable caramel and acid flavors is from 0.4 to 2.0 ppb. For the woody esters, higher concentrations are necessary.

On a dry coffee solids basis, the following concentrations are equivalent to the brew concentrations previously noted:

| Brew 1.35% Coffee Solids | Flavoring Concentration Dry Solids |
|---|---|
| ppb | ppb |
| 0.01 | 0.75 |
| 0.05 | 3.75 |
| 0.10 | 7.5 |
| 0.4 | 30 |
| 2.0 | 150 |
| 5.0 | 380 |
| 16.0 | 1200 |

The preferred concentration, particularly for dry soluble coffee, is 7.5 to 380 ppb, and more preferably from 30 to 150 ppb on a dry coffee solids basis.

The trans- form of the 2-nonenal and 2-nonenol and their derivatives are preferred because of isomeration, with time, of the cis- form. Of the trans- compounds the alcohol and acetal compounds are preferred over the aldehyde. The ester while stable requires higher concentrations to develop a woody flavor and is less preferred to the alcohol.

The flavor impact of the woody compounds and mixtures thereof is easily adjusted by varying the concentration of the flavoring compounds employed in the foodstuff. It is to be expected that adjustment will be necessary depending on the particular foodstuff being flavored. Initial panel screening, by those of ordinary skill in the art, is used to determine the threshold and proper strength level for the particular foodstuff in which the flavor is to be employed.

The 2-nonenal and 2-nonenol woody flavored compounds are particularly useful for balancing and blending the natural flavor of spray dried and freeze dried soluble coffee, decaffeinated coffee both soluble and regular, and regular coffee of various blends, particularly those having a high Robusta content. The flavor compounds are particularly preferred for imparting a woody flavor to the preceding coffees deficient in that flavor.

Again, even at levels below the woody threshold level, balancing of flavor is noted by expert tasters. These flavor compounds are also particularly useful when combined with steam generated natural coffee aromas or enhancers where there is produced a blending or smoothing of coffee aroma and flavor and a masking of the undesirable sourness and caramel characteristics often associated with coffee.

Similar flavor improvement is obtained by employing the woody compounds or mixtures thereof with synthetic coffee flavor compounds or with mixtures of synthetic and natural coffee aromas and flavors.

The woody compounds or mixtures thereof may be combined with foodstuffs or with edible diluents or carriers by art recognized methods. For example, a standard solution of trans-2-nonenal may be prepared by simply mixing the nonenal with alcohol, coffee oil or other diluents in which it is soluble. The woody flavor compounds thereof may also be incorporated in water by dissolution in a larger excess or by emulsification. They may also be incorporated in solid foodstuffs or carriers by forming a solution of the solid, adding the flavoring and drying by conventional techniques. Alternatively, a liquid dispersion or emulsion can be formed containing the flavoring and the foodstuff and the dispersion or emulsion dried to form a solid which may be ground if desired. For partially insoluble solids which contain water soluble solids, such as regular coffee, the woody compound may be incorporated in a liquid carrier, such as coffee or other vegetable oil, and sprayed or otherwise coated on the food as a film. Alternatively, the flavor compounds can be incorporated in a solid carrier and the carrier dry blended with the food. The technique employed is not critical, so long as there is obtained a uniform mixture of the flavoring compound and the foodstuff.

In addition to the application of the woody flavor compounds in foodstuffs, these flavoring agents may also be employed in edible substances, such as pharmaceuticals, where a woody, regular coffee note is desired.

The invention is now illustrated, but not limited by, the following examples:

EXAMPLE I

A. A mixture of one mole of nonanal, 2.5 moles of acetic anhydride, and 15 g. of anhydrous potassium acetate is refluxed for one hour and cooled. Excess acid is removed by a 2X wash with water, followed by 5% sodium carbonate wash to give 1-nonen-1-yl acetate as a relatively pure oil.

The oil is mixed with 200 ml of carbon tetrachloride and cooled in an ice bath. Bromine, diluted with an equal volume of carbon tetrachloride, is added slowly with agitation while maintaining the temperature below 10°C. Bromine addition is stopped when the bromine is no longer decolorized. To the brominated mixture, containing 1,2-dibromononen-1-yl acetate, is added 500 ml of methyl alcohol with shaking and cooling. The mixture is allowed to stand two days with occasional shaking and then diluted with 1.5 liters of water. The separated oil is washed with 5% sodium carbonate solution until free of acid and then fractionally distilled in the presence of a small amount of sodium carbonate to yield 2-bromo-nonanal dimethyl acetal.

The separated oil (one mole) is added to a mixture of 500 ml of methanol containing 2 moles of potassium hydroxide and 500 ml of butanol. The mixture is gently heated in a Claisen flask and the methanol allowed to distill off. When butanol begins to distill, the distillation is stopped and the contents transferred to a round-bottomed flask and refluxed in an oil bath. After refluxing for one hour, the mixture is washed with water and the oil fractionally distilled through a column in the presence of potassium hydroxide to yield 2-nonenal dimethyl acetal. F, B. Twenty to 30 ml of the recovered acetal is mixed with an equal volume of 50% citric acid solution and boiled gently in a Claisen flask. Methanol is allowed to boil off until the distillate temperature reaches 95°F , at which point distillation is stopped. The flask contents are 2X water washed, followed by a 5% sodium carbonate solution. The resulting oil is vacuum distilled to yield relatively pure trans-2-nonenal. Further purification is obtained, if desired, by gas chromatography.

C. Trans-2-Nonenal (8g., 0.056 mole), trimethylorthoformate (10.6 g., 0.1 mole), methyl alcohol (10ml.) and ammonium chloride (0.5 g.) are heated at reflux for 3 hours under nitrogen. The contents are cooled, filtered, diluted with water and extracted with ether. The ether layer is washed with 5% sodium bicarbonate followed by water and dried over sodium sulfate. Concentration and distillation gives trans-2-nonene dimethyl acetal, b.p. 50° – 64°C/0.5 mm., 5 g.

EXAMPLE II

Malonic acid (342 g, 3.3 mole) is dissolved in 555 ml of dry pyridine (slightly exothermic). The mixture is cooled in ice water and n-heptaldehyde (342 g, 3.0 mole) is added with stirring. After the addition is complete, the ice bath is removed and the mixture allowed to stand at room temperature for 60 hours, and then heated on a steam bath for 8 hours. The reaction mixture is poured onto an equal volume of water. The organic layer is separated, washed with 900 ml 25% HCl, taken up in benzene, washed with water and dried. Distillation under vacuum gave trans-2-nonenoic acid, b.p. 123°C/2 mm, 297 g, 64% yield.

A. Thionyl chloride (131 g, 1.1 mole) is added to trans-2-nonenoic acid (156 g, 1.0 mole). Reaction occurs immediately with the evolution of HCl and $SO_2$. After the initial reaction subsides, the mixture is heated slowly to 130°C. The dark mixture is vacuum distilled to yield trans-2-nonenoyl chloride, b.p. 90°C/2 mm, 155 g, 91% yield.

Trans-2-nonenoyl chloride (170 g, 1 mole) is dissolved in 500 ml of diglyme and placed in a flask fitted with a mechanical stirrer, dripping funnel, low temperature thermometer and nitrogen inlet and outlet. The flask is flushed with nitrogen and cooled to −78°C in a dry ice acetone bath. To the flask, lithium tri-t-butoxyaluminohydried (254 g, 1 mole) in 1000 ml of diglyme is added over a period of 7 hours. The cooling bath is removed and the contents of the flask are allowed to warm to room temperature. The contents are poured onto crushed ice and the oily layer taken up in ether. The ether solution is dried over sodium sulfate, concentrated and vacuum distilled to give trans-2-nonenal.

Trans-2-nonenal (7.0 g, 0.05 mole) is dissolved in 50 ml of ether and added to a solution of $LiAlH_4$ (0.54 g, 0.014 mole) in 50 ml of ether at such a rate to maintain gentle refluxing. When the addition is complete, the solution is refluxed for one hour. Ethyl acetate (2 ml) is added to destroy excess $LiAlH_4$. The mixture is acidified with 5M HCl. The ether layer is separated, washed 2X with water, and dried over sodium sulfate. The ether solution is concentrated and the residue vacuum distilled to yield trans-2-nonenol.

B. A 500 ml flask with a reflux condenser, mechanical stirrer and a dropping funnel, and protected from moisture with a drying tube is charged with $LiAlH_4$ (6.1 g, 0.16 mole) and 200 ml ether. A solution of trans-2-nonenoic acid (7.8 g, 0.05 mole) in 25 ml ether is added at a rate to maintain refluxing. Refluxing is continued for 1 hour and the mixture cooled. Exess reagent is destroyed by the addition of ethyl acetate (5 ml) followed by acidification with 5M HCl. The organic layer is separated, washed with water, dried and distilled under vacuum to give trans-2-nonenol.

EXAMPLE III

A. Sodium (5.8 g, 0.25 mole) is dissolved in liquid ammonia (500 ml) and 2-nonyne diethyl acetal (10.6 g, 0.05 mole) in ether (15 ml) is added dropwise to the solution over a thirty-minute period. The resulting mixture is stirred for two hours and then quenched with an ammonium chloride (16 g, 0.3 mole) and water (100 ml) solution. Ether (100 ml) is added and the organic layer separated and washed successively with 3% sulfuric acid solution, 5% sodium bicarbonate solution and water. The washed ether solution is dried over anhydrous sodium sulfate, concentrated and distilled to give 10 g. of trans-2-nonene diethyl acetal, b.p.69°–70°C/0.1 mm. The acetal is purified using gas liquid partition chromatography on diethylene glycol succinate.

B. Trans-2-Nonene diethyl acetal (21.4 g., 0.1 mole) is added to methanol (250 ml). A Lindlar type catalyst, 5% $Pd/BaSO_4$ (0.6 g) and quinoline (0.4 g) are added and the mixture placed on a mechanical skaker for 1 hour. The catalyst is filtered and the solvent distilled. The residue is distilled under vacuum yielding a mixture of the three acetals of nonenal, namely the diethyl, dimethyl, and ethylmethyl acetals. Separation by gas chromatography on a diethylene glycol succinate column gives trans-2-nonene ethyl methyl acetal.

EXAMPLE IV

Trans-2-nonenal (14.2 g, 0.1 mole), trimethylorthoformate (20 g, 0.13 mole), ethylene glycol (16 g, 0.25 mole) and ammonium chloride (0.5 g) are heated over a range of 90° – 125°C. Heating is continued until distillation of ethyl formate and ethanol stops (~20 ml). The mixture is diluted with water and extracted with ether. The ether extract is washed with 5% sodium bicarbonate water, dried over anhydrous sodium sulfate and concentrated. The residue is purified using gas liquid partition chromatography on OV-17, 180°C, to give trans-1-octenyl-2-dioxolane.

EXAMPLE V

2-Nonyn-1-ol (20 g, 0.4 mole) in 200 ml methyl alcohol is hydrogenated in a Parr bomb using a Lindlar catalyst (0.5 g $Pd/BaSO_4$) and quinoline (0.5 g). The hydrogenation was monitored by gas liquid partition chromatography on diethylene glycol succinate. Hydrogenation is stopped when the concentration of the acetylenic alcohol equals that of the saturated alcohol. The hydrogenation mixture is filtered, diluted with water and extracted with ether. The ether extract is dried over anhydrous sodium sulfate, concentrated and distilled to yield 13 g of cis-2-nonen-1-ol, b.p. 60°–64°C/0.5 mm.

EXAMPLE VI

A. Cis-2-nonenol (5 g, mole) is stirred with manganese dioxide (50 g, mole) in ether (250 ml) at room temperature for 1 hour. The mixture is filtered, ether removed, and the residue distilled to give cis-2-nonenal.

B. Cis-2-nonenol (2.9 g, 0.03 mole), acetic anhydride (3.1 g, 0.045 mole) and pyridine (15 ml) is heated at reflux for 3 hours. The solution is cooled and diluted with water. The organic layer is separated and washed successively with 3% sulfuric acid, and water. The solution is dried over sodium sulfate and distilled under vacuum to yield cis-2-nonenyl acetate, b.p. 58° – 62°C/0.1 mm.

EXAMPLE VII

Isobutyric acid (22.0 g, 0.25 mole), trans-2-nonen-1-ol (44.3 g, 0.25 mole), xylene (100 ml) and p-toluenesulfonic acid are heated to 145°C. The solution is refluxed for 5 minutes and 4.5 ml water is collected by distillation. The reaction mixture is cooled and first washed with water followed by 5% sodium carbonate. The washed solution is dried over sodium sulfate and distilled to yield 34.1 g of trans-2-nonenyl isobutyrate, b.p. 87°–88°C/0.5 mm. An analytical sample is obtained for taste evaluation using gas chromatography.

EXAMPLE VIII

To a flask equipped with a reflux condenser, mechanical stirrer and dropping funnel is added trans-2-nonenol (14.2 g, 0.1 mole), $N_1N$-dimethylaniline (12 g, 0.1 mole) and 20 ml ether. To the stirred mixture is added dropwise phenylacetyl chloride (15.5 g, 0.1 mole) at a rate to maintain a vigorous reflux of ether. After the addition, the mixture is warmed on a water bath for 2 hours and then allowed to stand several hours. The ether layer is separated from the precipitate and extracted with 10% sulfuric acid. The ether layer is dried over anhydrous sodium sulfide and purified up to give trans-2-nonenyl phenylacetate.

EXAMPLE IX

A. Formic acid (142 g, 3 moles) and acetic anhydride (400 g, 4 moles) are mixed and allowed to stand overnight. The mixture is then heated to 50°C and maintained for 1 hour at 50°C. The resulting product is distilled under vacuum to give acetyl formate, 395 g, b.p. 46°–50°C/46 mm.

B. Acetyl formate (39.6 g, 0.45 mole) is added dropwise to a cooled mixture of sodium formate (6.8 g, 0.10 mole) and trans-2-nonen-1-ol (47.3 g, 0.33 mole). When the addition is complete, the reaction mixture temperature is maintained at 60°C for 7 hours. The mixture is cooled and diluted with water. The organic layer is separated and washed with 5% sodium bicarbonate, water and then dried over sodium sulfate. Trans-2-nonenyl formate, 419 g is obtained on distillation, b.p. 60°–5°C/50-55 mm.

EXAMPLE X

Pyridine (100 ml) and trans-2-nonen-1-ol (28.4 g, 0.2 mole) are heated to 110°C and acetic anhydride (30.6 g, 0.3 mole) is added dropwise. The reaction mixture is maintained at 110°–115° for 2 hours and 120°–125°C for 3 hours. The mixture is cooled and washed with water, 5% sulfuric acid, and finally water. The solution is dried over sodium sulfate. Trans-2-nonenyl acetate, 33.0 g is obtained by vacuum distillation, b.p. 70°–5°C/50-55 mm.

EXAMPLE XI

A. A taste comparison was made of instant Maxwell House brand coffee beverage containing 1.35% coffee solids enhanced with 1 ppb and 2 ppb trans-2-nonenal. When compared to control, the 2 ppb enhanced sample had an improved woody regular coffee flavor and lacked the typical caramel and acid notes of the control. The 1 ppb enhanced sample did not give a detectable woody flavor, but did balance or blend the coffee flavor and masked the caramel and acid flavor of the control.

B. Example XIA was repeated employing a broader range of flavor enhancement. Expert tasters made the following comments compared to control:

| Concentration of trans-2-nonenal in the brew | Flavor Comments |
|---|---|
| ppb | |
| 0.2 | detectable subtle flavor |
| 0.4 | subtle recognition of woodiness |
| 0.6 | definite recognition of woodiness |
| 1.0 | woody and smoother |
| 2.0 | woody and groundsy |
| 8.0 | high woody impact |
| 16.0 | tallowy flavor |
| 30.00 | burnt, fatty |
| 40.0 | burnt, fatty and rancid |

C. Example XIB was repeated with the trans-2-nonenal replaced by trans-2-nonenol:

| Concentration of trans-2-nonenol in the brew | Flavor Comments |
|---|---|
| ppb | |
| 0.2 | less caramel than control |
| 0.4 | slightly more apparent than above |
| 0.6 | smoother and slightly woody with caramel notes masked |
| 1 | smoother, greater woody impact |
| 2 | clean and woody |
| 8 | very woody |
| 16 | flavor character changing with fatty after-taste apparent |
| 20 | fatty and harsh |
| 40 | same |
| 60 | same |

The flavor impact of the other woody flavor compounds employed in this invention is determined in the same manner.

EXAMPLE XII

Spray dried instant Maxwell House brand coffee containing a synthetic, winey, buttery flavor was compared to an identical sample containing an additional 2ppb trans-2-nonenal. The comparison was made by preparing a 1.35% coffee solids brew and then adding from a dilute standard solution sufficient trans-2-nonenal to give 2 ppb concentration in one of the two brews.

The sample treated with trans-2-nonenal was found to have a very desirable balanced flavor, having prominent winey, buttery and woody regular coffee notes. The trans-2-nonenal sample had a far better balanced flavor, the nonenal apparently blending the desirable flavors while masking undesirable flavors.

A similar flavor effect is obtained when trans-2-nonenal is replaced by trans-2-nonenol, cis-2-nonenol or the acetal or ester derivatives described herein.

EXAMPLE XIII

A comparison similar to Example XI was made using freeze dried Maxim brand soluble coffee. The cup enhanced with 2 ppb trans-2-nonenal had an improved woody regular coffee note. In addition, the typically winey and buttery notes of the coffee were better balanced and the typical sourness of the brew was masked. At 1 ppb, while woodiness was not evident, there was an improved balanced cup flavor and a reduction in sourness.

When expert tasters compare either trans-2-nonenal or trans-2-nonenol at the 1 ppb and 2 ppb level, similar improvement in winey and buttery notes is apparent as well as a definite woody flavor. Similar taste effects are noted for the other woody flavor compounds of this invention.

EXAMPLE XIV

A comparison similar to Example XII was made using freeze dried Maxim brand soluble coffee having fixed therein a fraction of steam generated aroma (WD-3 SVF) which contains woody regular coffee notes. Addition of 2 ppb of trans-2-nonenal produced a very good regular coffee flavor, the brew having improved cup flavor and lacking sourness when compared to the control.

A similar result is obtained when trans-2-nonenol is substituted for the trans-2-nonenal employed in Example XIV.

EXAMPLE XV

A. A comparison similar to Example XI was made of spray dried instant Maxwell House soluble coffee, having added to the 1.35% coffee solids brew lppb each of 2-methoxy-3-isobutyl pyrazine and trans-2-nonenal. Compared to control, the enhanced brew had a more rounded flavor containing more regular coffee notes.

B. When the above comparison is repeated employing different levels of the flavor additives, the following results are obtained:

| Flavor Concentration in the Brew | | Flavor Comments |
|---|---|---|
| trans-2-nonenal | 2-methoxy-3-isobutyl pyrazine | |
| ppb | ppb | |
| 1.0 | 0.5 | woody, subtle earthly flavor, slightly green |
| 4.0 | 0.5 | good balance, less astringent, smooth and groundsy |
| 3.0 | 1.5 | earthy, woody |
| 2.0 | 1.0 | woody, subtle earthy flavor, slightly green |

C. When trans-2-nonenal is replaced by trans-2-nonenol, similar flavor changes are obtained.

D. When 2-methoxy-3-isobutyl pyrazine is replaced by other

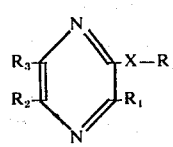

wherein X is oxygen or sulfur, preferably oxygen, R is lower alkyl, preferably having one to three carbon atoms and $R_1$, $R_2$ and $R_3$ hydrogen or alkyl provided at least one of $R_1$, $R_2$ and $R_3$ is alkyl of two to twelve carbons, preferably three to five carbons, similar green notes are imparted to the trans-2-nonenal or trans-2-nonenol flavored brew.

E. When a test similar to XVB is made employing freeze dried Maxim soluble coffee at 1.35% coffee solids brew, the following flavor characteristics are noted:

| Flavor Concentration in the Brew | | Flavor Comments |
|---|---|---|
| trans-2-nonenal | 2-methoxy-3-isobutyl pyrazine | |
| ppb | ppb | |
| 0.25 | 0.025 | nice cup flavor with winey, buttery notes and a slight woody flavor |
| 0.25 | 0.175 | earthy note is too prominent, masking the winey notes |
| 0.5 | 1.0 | too earthy and green |

EXAMPLE XVI

A ten percent ethanolic solution of trans-2-nonenal (Compagnie Parento, Croton-on-Hudson, New York) was passed through a Perkin-Elmer model 900 gas chromatography unit having a 6-foot by 1/8 inch column packed with 10% diethylene glycol succinate polyester on 80/90 Anakrom ABS. The major component representing trans-2-nonenal was collected, diluted with water and vigorously shaken to give a 40 ppm standard solution. This material was evaluated in water at 2 ppb and 20 ppb and found to give a regular coffee flavor characterized by experts as woody or spent grounds. Similar results were obtained for tests in soluble coffee.

Expert tasters find undesirable flavors at about 16 ppm for both trans-2-nonenal and trans-2-nonenol which are not apparent to less skilled tasters.

EXAMPLE XVII

An expert panel flavor evaluation was made of trans-2-nonenal, purified as in Example XVI, at a level of two parts per billion in instant Maxwell House brand soluble coffee at a 1.35% coffee solids concentration. The panel initially found a slight spent grounds flavor which improved the regular brewed character of the coffee. The panel noted a desirable blending or mixing of flavor and a secondary aromatic flavor similar to that produced by the addition of steam generated aroma.

EXAMPLE XVIII

A flavor comparison, similar to Example XI, was made using spray dried Sanka brand decaffeinated soluble coffee having added thereto 2 ppb of trans-2-nonenal. Compared to control, the flavor enhanced brew had an improved woody flavor and good balance of cup flavor and aroma.

When trans-2-nonenal is replaced by trans-2-nonenol, or the acetal or ester derivatives employed herein or cis-2-nonenol, there is obtained a similar flavor improvement.

EXAMPLE XIX

Two hundred pounds of whole roasted coffee are introduced into a commercial oil expeller and expressed. Sixteen pounds of oil are obtained, which are clarified by filtration. Twelve pounds of clarified oil and 4 pounds of fines are obtained. The clarified oil is stored at 50°F under carbon dioxide until ready for use.

The expeller cake resulting from the expression of the coffee is pelletized. The pellets are added to 800 pounds of roasted and ground coffee. The mixture is introduced into a conventional commercial coffee extractor and is extracted with 3,000 pounds of water under conventional coffee percolation techniques used in soluble coffee production. Three hundred pounds of soluble solids are extracted and collected as a liquid extract weighing 900 pounds. The extract is cooled to 60°F and 720 pounds of the extract are then spray dried by conventional coffee spray drying to obtain a soluble coffee powder having 3% moisture. The remaining 180 pounds of the extract are divided into two 90 pound portions. Six pounds of the expressed oil are warmed to 65°F and dispersed in 90 pounds of extract by homogenization at 2,000 psig. Fifty milligrams of trans-2-nonenal, dispersed in a liter of water, are added to the other 90 pounds of extract and mixed. The two 90 pound batches are then combined and frozen at a thickness of one-eighth inch in trays in a period of about one hour to a temperature of −30°F. The frozen mixture of extract and aromas is then freeze dried in a commercial freeze drying unit. The freeze concentrate is then combined with the spray dried powder.

Instead of freeze drying the aroma concentrate, it may be spray dried and then blended in a similar manner.

Instead of employing freeze dried coffee as the carrier for the trans-2-nonenal, the flavor may be incorporated in a film forming substance, dried and ground to a fine powder. The powdered concentrate may then be dry blended with the spray dried soluble coffee prepared as above.

Example XIX may be modified to produce a soluble coffee having trans-2-nonenal incorporated throughout all of the soluble powder. The entire 900 pounds of extract are collected and 40 milligrams of trans-2-nonenal in 2 liters of aqueous 5% ethanolic solution added thereto and blended by mixing until a homogenous mixture is obtained. The extract-trans-2-nonenal mixture is then spray dried or freeze dried to produce a flavor enhanced soluble coffee.

When the above processes are repeated employing trans-2-nonenol for trans-2-nonenal, there is obtained aromatized coffee products.

EXAMPLE XX

Trans-2-nonenal (5 mg in one ml of ethanol) is added to 500 ml of distilled water and the aqueous mixture poured into 52 pounds of coffee extract of 28.2% coffee solids. The coffee-nonenal mixture is stirred and then poured into trays and frozen to form 3/8 inch thick slabs. Control slabs are also prepared from the same extract without the addition of flavors.

The slabs are freeze dried in a 50 square foot Stokes Freeze Drier under 150 microns pressure. The freeze drier shelf temperature is lowered from 22° to 8°C during the first 15 minutes of drying, then raised progressively to 50°C during the next 45 minutes of drying and then progressively lowered to 30°C over the next 22 hours of drying. Condenser temperature is maintained at −40°F.

The dry product is removed from the drier, broken up and stored.

A flavor evaluation is made by dissolving 0.65 gms of trans-2-nonenal aromatized freeze dried coffee and 2.60 gms of freeze dried control in eight bunces of hot water to give a theoretical 2 ppb concentration. Control cups are prepared by dissolving 3.25 gms of freeze dried control coffee in eight ounces of hot water and adding thereto 10 microliters of a 5 ml aqueous solution containing 0.25 mg trans-2-nonenal to give a 2 ppb concentration.

The freeze dried aromatized sample was judged to contain about ninety percent of the woody flavor of the control, indicating a slight loss of trans-2-nonenal aroma during freeze drying.

Trans-2-nonenal is replaced by trans-2-nonenol and the above procedure repeated to produce aromatized freeze dried coffee.

EXAMPLE XXI

To 500 ml of distilled water is added 2.34 mg of trans-2-nonenal dissolved in 1 ml of ethanol. The aqueous mix is added to 40 pounds of coffee extract (24.5% solids) and the mixture is spray dried.

Unaromatized extract is spray dried umder equivalent conditions for use as a control. A flavor evaluation is made by dissolving 3.25 g of the aromatized coffee in eight ounces of hot water. Control cups are prepared by dissolving in each cup 3.25 g of control coffee in eight ounces of hot water and then adding thereto 10 microliters of a solution of 0.24 mg trans-2-nonenal in 5 ml of water.

A triangular, odd cup flavor evaluation found no difference between the cups, indicating no significant loss of trans-2-nonenal during spray drying.

EXAMPLE XXII

To 25 grams of Wesson oil is added 1.75 milligrams of trans-2-nonenal. The resulting mixture is added to a solution of 500 grams of gum arabic dissolved in one liter of water. The mixture is emulsified and spray dried to give a concentrate.

The concentrate is blended at a 5% by weight level with foodstuffs such as spray dried and freeze dried soluble coffee to enhance the regular coffee flavor of beverages produced from these soluble coffees.

When trans-2-nonenal is replaced with trans-2-nonenol a concentrate is obtained, which when added to coffee gives enhanced coffee flavor.

EXAMPLE XXIII

One mole of alpha cyclic dextrin is dissolved in 5 liters of warm water. To the resulting solution is added one-half mole of trans-2-nonenal and the mixture is shaken vigorously overnight. The mixture is frozen and freeze dried in a laboratory drier to yield a flavor fixed concentrate. The concentrate may be dry blended with a diluent and then employed where large batches of foodstuff are to be coffee flavored.

EXAMPLE XXIV

A flavor comparison similar to Example XI is made using 100% Robusta spray dried soluble coffee having added thereto 2 ppb of trans-2-nonenal. Compared to control, the flavor enhanced brew had an improved woody cup flavor and aroma.

When trans-2-nonenal is replaced by 2 ppb of trans-2-nonenol, there is obtained a similar woody flavor and aroma.

EXAMPLE XXV

To various foodstuffs is added minute amounts of the enhancing compounds of this invention at the proportions indicated. The foodstuffs are then evaluated by comparison to a control not containing the enhancer. Results are reported in the following table.

TYPICAL EVALUATION OF
2-NONENE-1-AL AND 2-NONENE-1-OL IN VARIOUS PRODUCTS

| Ex. No. | Product | 0.12 ppb | 0.25 ppb | 0.5 ppb | Concentration of Trans-2-nonene-1-al 1 ppb | 2 ppb | 4 ppb |
|---|---|---|---|---|---|---|---|
| 1 | Cola beverage | | | | Enhanced cola flavor More like "Coke" Nice, woody flavor | Woody | |
| 2 | Pear nectar | | | | Increased pear flavor | | |
| 3 | Ginger ale | | | | Enhanced ginger ale flavor Slight woody flavor | Woody | |
| 4 | Black cherry gelatin dessert | | | | Slight woody character | Smoother flavor Woody | |
| 5 | Cranberry juice | | Slightly less astringent | | Less astringent Woody | Woody | |
| 6 | Vanilla instant pudding | | | | | | More vanilla More natural Nice woody |
| 7 | Condensed beef broth | | Fuller flavor, meatier, smoother | Meatier and smoother | More vegetable character More roasted character Smoother flavor | High woody | |
| 8 | Root Beer beverage | | | | Enhanced flavor | High woody | |
| 9 | Creme Soda | | | | More creme character Woody | High woody | |
| 10 | Maple and sugar syrup | | | | | | More maple More buttery Woody character |
| 11 | Cherry gelatin dessert | | Better flavor balance, smoother flavor | | More natural than control Eliminates cheap candy cherry character Smoother Definite improvement | Woody | |
| 11a | Artificially sweetened cherry gelatin | | More flavor | Smoother better balanced flavor | | | |
| 12 | Artificially sweetened cola beverage | | | | Higher cola flavor Smoother flavor Higher apparent carbonation | Woody | |
| 13 | Meat broth | | | | Higher flavor impact | More meaty but unbalanced | |

| Ex. No. | Product | 1.2 ppb | 2.5 ppb | 5.0 ppb | Concentration of Trans-2-nonene-1-ol 10 ppb | 20 ppb | 40 ppb |
|---|---|---|---|---|---|---|---|
| 14 | Cranberry juice | | Less astringent, enhanced flavor | | Reduced astringency Less acid impact Definite improvement | Less astringent Woody | |
| 15 | Maple and sugar syrup | | | | | | More maple Covers undesirable harsh character of product Smoother |
| 16 | Meat Broth | | | | Higher flavor intensity | Beefier, meatier but fatty | |
| 17 | Artificially sweetened cherry gelatin | | | Smoother balanced flavor | | | |

EFFECT OF COMBINATION OF
2-NONENE-1-AL AND 2-NONENE-1-OL

| Ex. | Product | Control | Evaluation |
|---|---|---|---|
| 18 | SS Pierce Cranberry Juice | Tart, Astringent Cranberry | 0.13 ppb Nonene-1-al + 1.3 ppb Nonene-1-ol |

EFFECT OF COMBINATION OF 2-NONENE-1-AL AND 2-NONENE-1-OL -continued

| Ex. | Product | Control | Evaluation |
|-----|---------|---------|------------|
| | | | Less stringent |
| | | | 0.25 ppb Nonene-1-al + 2.5 ppb Nonene-1-ol |
| | | | Less stringent |
| | | | More Cranberry |

While the characteristic woody flavor of the enhancers are acceptable in some of the foodstuffs tested, the enhancers may be added at below the flavor threshold concentration. For example, the concentration of 2-nonene-1-ol added to cranberry juice should be about 10 ppb and not 20 ppb where the woody character of the enhancer becomes prominent.

EXAMPLE XXVI

A solution of trans-2-nonenal was prepared by dissolving 20 mg of the aldehyde in 50 ml of ethanol. One half of a milliliter of the resulting solution was then dissolved in 50 ml of spring water to yield a 0.2 mg/50 ml solution. The spring water solution was employed to prepare enhanced instant Postum by adding a sufficient amount to two grams of Postum dissolved in 200 ml of boiling spring water to give 5, 10, 20, and 30 ppb concentrations of nonenal in the hot Postum beverage. These beverages were compared with a control of 2 grams Postum dissolved in 200 ml boiling spring water by several expert tasters. The samples containing 5 ppb and 10 ppb nonenal were preferred. The nonenal reduced appreciably the characteristic molasses flavor of Postum and imparted a slight woody flavor. There was a significant reduction in the sweet, cereal taste of the beverage. When trans-2-nonenol is employed, similar results are obtained.

Obviously, many modifications and variations of the present invention are possible in light of the above teachings. It is therefore understood that, within the scope of the appended claims, the invention may be practiced otherwise than as specifically described.

We claim:
1. A process for enhancing the flavor of foodstuffs comprising adding thereto a mixture formulated to give a coffee-like flavor to said foodstuff of:
   a. a compound selected from the group consisting of 2-nonenal, 2-nonenol, lower alkyl acetals of 2-nonenal, esters of organic acids and 2-nonenol in which the carbonyl is not conjugated with a double bond or aromatic ring, and mixtures thereof in an amount effective to impart woody coffee-like flavor to the foodstuff; and
   b. a compound represented by the formula:

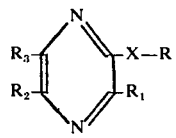

wherein X is oxygen or sulfur, R is a lower alkyl, and $R_1$, $R_2$ and $R_3$ hydrogen or alkyl provided at least one of $R_1$, $R_2$, and $R_3$ is alkyl of two to twelve carbons, and mixtures thereof in an amount effective to impart green flavor to the foodstuff said mixture being added in an amount effective to enhance the coffee flavor of the foodstuff.

2. The process of claim 1 wherein said foodstuff is coffee.
3. The process of claim 2 wherein said compound of a) is trans-2-nonenal.
4. The process of claim 2 wherein said compound of b) is 2-methoxy-3-isobutyl pyrazine.
5. The process of claim 3 wherein said compound of b) is 2-methoxy-3-isobutyl pyrazine.
6. The process of claim 5 wherein said coffee is coffee extract.
7. The process of claim 5 wherein said coffee is soluble coffee.
8. A foodstuff having added thereto as an active flavor ingredient a mixture formulated to give a coffee-like flavor to the foodstuff comprising:
   a. a compound selected from the group consisting of 2-nonenal, 2-nonenol, lower alkyl acetals of 2-nonenal, esters of organic acids and 2-nonenol in which the carbonyl is not conjugated with a double bond or aromatic ring, and mixtures thereof in an amount effective to impart body coffee-like flavor of the foodstuff; and
   b. a compound represented by the formula:

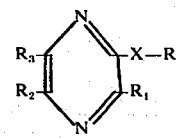

wherein X is oxygen or sulfur, R is a lower alkyl, and $R_1$, $R_2$, and $R_3$ hydrogen or alkyl provided at least one of $R_1$, $R_2$, and $R_3$ is alkyl of two to twelve carbons in an amount effective to impart a green flavor to the foodstuff; said mixture added in an amount sufficient to enhance the coffee flavor of the foodstuff.

9. The foodstuff of claim 8 wherein the foodstuff is coffee.
10. The foodstuff of claim 8 wherein the foodstuff is soluble coffee.
11. The foodstuff of claim 10 wherein the compound of a) is trans-2-nonenal.
12. The foodstuff of claim 10 wherein the compound of b) is 2-methoxy-3-isobutyl pyrazine.
13. The foodstuff of claim 11 wherein the compound of b) is 2-methoxy-3-isobutyl pyrazine.

* * * * *

UNITED STATES PATENT AND TRADEMARK OFFICE
CERTIFICATE OF CORRECTION

PATENT NO. : 3,962,321
DATED : June 8, 1976
INVENTOR(S) : Thomas H. Parliment, et al It is certified that error appears in the above—identified patent and that said Letters Patent are hereby corrected as shown below:

In Column 1, Line 24 change "threeof" to ---thereof---.

In Column 9, Line 3 after "acetal." delete ---F,---.

In Column 20, Line 39 (Claim 8, sub-section a., line 6) change "body" to ---woody---.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*